US00PP11938P2

(12) United States Plant Patent
McCommon

(10) Patent No.: US PP11,938 P2
(45) Date of Patent: Jun. 19, 2001

(54) *RAPHIOLEPIS INDICA* PLANT NAMED 'CONYNNE'

(75) Inventor: Becky Lynne McCommon, Winter Garden, FL (US)

(73) Assignee: Plant Development Services Inc., Loxley, AL (US)

( * ) Notice: Subject to any disclaimer, the term of this patent is extended or adjusted under 35 U.S.C. 154(b) by 0 days.

(21) Appl. No.: 09/306,884

(22) Filed: May 7, 1999

(51) Int. Cl.[7] ..... A01H 5/00
(52) U.S. Cl. ..... Plt./254
(58) Field of Search ..... Plt./254

*Primary Examiner*—Bruce R. Campell
*Assistant Examiner*—Anne Marie Grünberg

(57) ABSTRACT

A new and distinct variety of *Raphiolepis indica* found as a chance sport on a seedling *Raphiolepis indica* plant of unknown parentage. The new variety is unique with its compact growth habit and attractive single to semi-double, strong pink flowers.

1 Drawing Sheet

BACKGROUND OF THE INVENTION

This new Raphiolepis variety was found in May, 1991 as a chance sport on an unnamed unpatented seedling *Raphiolepis indica* plant of unknown parentage. The plant upon which the sport was found is not a horticultural variety and is not available commercially. The sport, hereinafter referred to as 'Conynne', was discovered by the late Clayton J. McCommon in a cultivated area at Avalon Ornamentals, 16515 Davenport Road, Winter Garden, Fla. The new and distinct *Raphiolepis indica* plant of this invention comprises a novel and valuable plant with a dense, low spreading habit and an abundance of pink flower clusters. The new variety has retained many of the outstanding attributes of its parent species, in particular its tolerance of heat, drought, salt, and disease which makes it adaptable to culture in most of the Sunbelt States. As with the parent species, the plant of this invention may be advantageously employed as a specimen appointment, a ground cover, in either formal or informal groupings, and is quite attractive in mass plantings. 'Conynne' serves well in foundation plantings and is adapted for culture as a potted plant. 'Conynne', is responsive to pruning and training and may be employed in forming dense, attractive, low-growing hedges, and maintained without an excessive amount of care. This plant is easy to care for and maintain in size due to its short internodes, slow to moderate growth rate, heavy branching, and dense canopy. Its natural propensity to remain small to maturity makes it valuable for landscape uses in smaller home gardens which require plants which do not outgrow their intended mature dimensions.

Asexual propagation of the new plant by cuttings has been under Mrs. McCommon's direction at Avalon Ornamentals in Winter Garden, Fla. Several generations of the new plant have been evaluated and the distinctive characteristics of the plant have remained stable. The plant cannot be reproduced true from seed.

SUMMARY OF THE INVENTION

The following are the most outstanding and distinguishing characteristics of this new cultivar when grown under normal horticultural practices in Winter Garden, Fla.

1. Dense, low, and spreading in nature. Plant is wider than tall.

2. Moderate to slow growth rate.

3. New growth terminals are pronounced with a light bronze coloration which offers a novel and strikingly appealing contrast of new foliage to old foliage in plants of this market class.

4. Hardy to Zone 7.

5. Heat and drought resistant.

6. Good plant for coastal areas because of wind and salt tolerance.

7. Good specimen plant.

8. Good foundation plant.

9. Very desirable in planters.

10. Produces seeds and therefore may result in bird visitations.

11. Makes a very good low growing hedge.

12. Flowers are single to semi-double, pink, fragrant, and profuse.

DESCRIPTION OF THE DRAWINGS

This new *Raphiolepis indica* variety is illustrated by the accompanying photographic prints in which.

1.

2.

Figure 1:
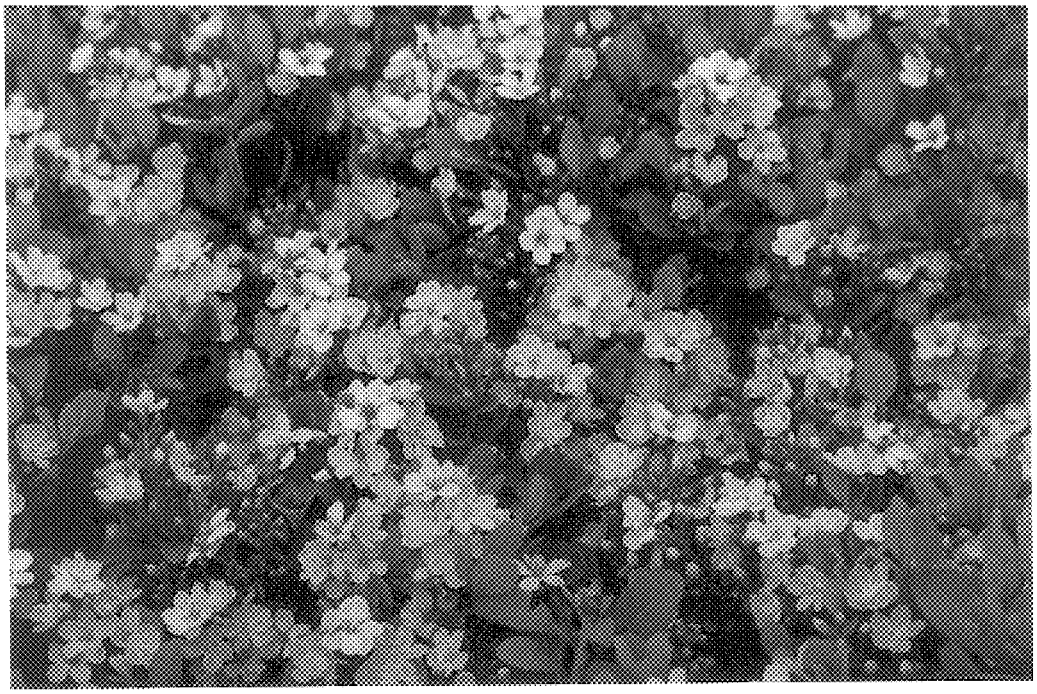
FIG. 1 is a close-up showing flower, buds, foliage, and stem color as well as flower size and form.
Figure 2:
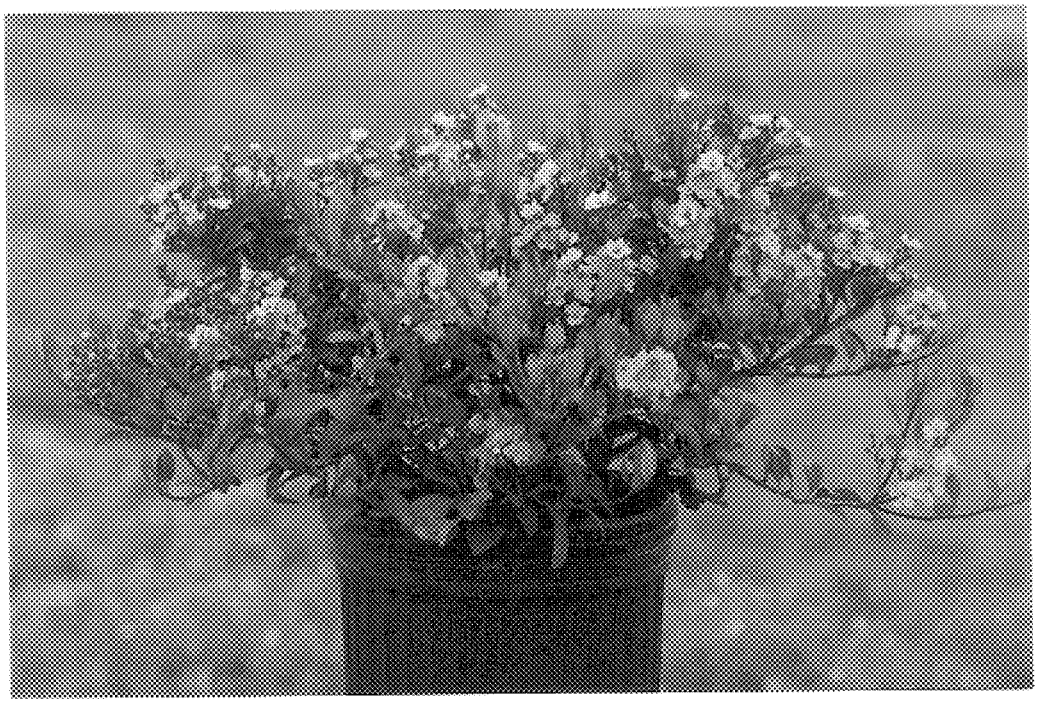
FIG. 2 shows the dense, low, and spreading growth habit of a three gallon plant.

The colors shown are as true as is reasonably possible to obtain by conventional photographic procedures. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of Raphiolepis based on my observations made of plants grown in commercial production practices, in greenhouses, and in established landscape plantings in Winter Garden, Fla.

| Distinctive Characteristics: | | | |
|---|---|---|---|
| Characteristic | 'Conynne' | 'Conor' | 'Jack Evans' |
| Height (Mature) | 2–3' | 3–4' | 4–5' |
| Width (Mature) | 3–4' | 4–5' | 4' |
| Leaf Length | 1¾–2⅝" | 2–3" | 2–3" |
| Leaf Width | ¾–1" | 1–1¼" | 1–1½" |
| Leaf Margin | Serrate-Crenate | Serrate-Crenate | Entire |
| Leaf Tip | Acute | Acute | Obtuse |
| Leaf Curviture | Almost Flat | Undulate w/Revolute Margins | Reflexed Tip |
| Flower | Single to Semi-Double | Semi-Double | Single |
| Flower Color | Red-Purple G. 68B | Red-Purple G. 65B | Red-Purple G. 62B |
| Petal Number | 5–8 | 5–8 | 5 |
| Petal Shape | Obovate | Oblanceolate | Elliptical |

The plant from which all above varieties originated has the botanical name Rosaceae *Raphiolepis indica*. The author of the genus name Raphiolepis is John Lindley (1799–1865). The original author of the species name Indica is Carlolus Linnaeus (1707–1778) and the name was transferred to the plant *Raphiolepis indica* by John Lindley.

The new variety 'Conynne' was found in 1991 as a natural variation (sport) of a seedling *Raphiolepis indica*. It is sold under the Trademark name Becky Lynne and is listed as *Raphiolepis indica* Becky Lynne TM 'Conynne'. 'Conynne' differs from the parent species *Raphiolepis indica* in that it is a uniformly compact plant with pink flowers (Red-Purple Group 68B).

*Raphiolepis indica* 'Conor' U.S. Plant Pat. No. 9,398 and the non-patented variety *Raphiolepis indica* 'Jack Evans' are well known in the industry and are comparable to 'Conynne' in that all are compact growers with pink flowers. However, there are many differences. 'Conynne' is naturally very bushy and dense due to its shorter internodes. This results in a shorter, more compact plant. The foliage of the new variety is smaller and almost flat. 'Conynne' also has a darker pink flower with obovately shaped petals.

Classification:

*Botanic.*—*Raphiolepis indica* 'Conynne'.

*Form.*—Low, compact and spreading.

*Height.*—2–3'.

*Width.*—3–4'.

*Growth rate.*—In a period of six years from a rooted cutting the plant reaches a height of 2 feet and spread of 3 feet under normal growing conditions in Winter Garden, Fla. The plant normally grows at the rate of about 4 inches or more per year and reaches a height of 3 feet and spread of 4 feet at maturity while maintaining a dense habit due to the abundant branch development.

*Growth habit.*—Low, compact and spreading evergreen shrub. Moderate to slow growth rate under normal fertilization and moisture conditions.

*Foliage.*—Alternate, simple, evergreen, elliptic to slightly obovate, almost flat, and varying in size from 1¾" to 2⅝" long and ¾ to 1" wide. The margins are serrate to crenate, with a petiole ¼" to ½" long. The midrib is prominent on both sides of the leaf and the smaller veins are prominent on the underside. Veins are depressed on the upper side giving a leathery appearance. These upper veins are Yellow-Green Group 146C. The base of the leaf is attenuate to cuneate and the apex is acute. The upper surface of the mature leaf is Yellow-Green Group 147A, glossy, and glabrous. The underside is Yellow-Green Group 146C and matte. The underside veins are Yellow-Green Group 146A. These mature leaf colors are persistent throughout the winter. The immature leaves are tomentulose and pronounced with a light bronze coloration Yellow-Group 152D which changes to Yellow-Green Group 147A in 3 to 4 weeks in Winter Garden, Fla. The paired foliaceous stipules are 3/16–⅜" long and 1/16–⅛" wide. The upper surface is Yellow-Green Group 145A and the underside is Yellow-Green Group 145B. The stipules are caducous.

In 1996, the date of initial spring growth was February 20, in Winter Garden, Fla. After the initial spring flush, there was almost continuous slow growth until fall, ending November 1, also in Winter Garden, Fla. When grown in full sun, the internode length of this plant is ⅜" to ⅝". When grown in light shade, the internode length is ½" to ⅞". As would be expected, a plant grown in the shade results in a taller, less dense plant with larger leaves.

*Stems.*—The young shoots have a reddish pigmentation, Greyed-Purple Group 183A and are tomentulose. The base of the immature petioles are also Greyed-Purple Group 183A. After one or more years, the stems are generally grey (Greyed-Green Group 197B), glabrous and rugose. The pith is solid and uniform.

*Flowers.*—Perfect, single to semi-double, pink, Red-Purple Group 68B front, Red-Purple Group 62C back and edges, ¾" diameter, fragrant, borne on dense, upright, tomentulose, 3–4" high and wide terminal panicles from March to April. As flowers mature they fade to Red-Purple Group 62D and White Group 155C. Each panicle has from 3–6 racemes which have from 1–10 flowers each, resulting in 50 or more flowers per panicle. A mature plant can have 100 or more panicles. The flowers are attached to short pedicels which are ⅛" to ¼" in length and Yellow-Green Group 146D. The peduncle of each raceme is from ⅜" to ½" long and Yellow-Green Group 146D. Each flower has 5–8 petals that are ⅜" long and 5/16" wide, obovate, and have obtuse tips. The flower has from 15 to 20 stamens, 3/16" long, with anthers Yellow Group 9C. The pollen matures to Yellow Group 8B. The pistil is ¼" long, White Group 156C, and consists of 2 styles which are united and have ciliate margins. In 1996, the blooming period began March 2, in Winter Garden, Fla. and ended April 30. The self cleaning blooms last 5 to 7 days on the plant in the garden. Some blooms will appear in May through October in the Southeastern United States.

*Fruit.*—Drupaceous, globose, ¼" to ⅜" in diameter, 1 to 2 seeded. Summer fruit color Yellow-Green Group 144A ripens to Greyed-Purple Group 187A in the fall and persists as Black Group 202A attractively through the winter. Mature seeds are Greyed-Orange Group 163A beneath the pericarp.

*Culture.*—Grows well in a wide range of conditions and tolerates sun to part shade. Grows in nearly any soil type, from moist to very dry and sand to clay. Responds well to mulching and medium applications of fertilizer; prefers ph 6 to 7. Very little pruning is needed. Adaptable to containers and above ground planters. Ideal for coastal regions and warmer parts of the Piedmont. Tolerates wind and salt spray. Progagated with semi-hardwood cuttings in late spring through the summer.

*Pests.*—Scale and spider mites can be a problem.

I claim:

1. A new and distinct variety of Raphiolepis plant named 'Conynne' as herein described and illustrated.

* * * * *